(12) United States Patent
Seo et al.

(10) Patent No.: US 11,698,952 B2
(45) Date of Patent: Jul. 11, 2023

(54) SMART HARDWARE SECURITY ENGINE USING BIOMETRIC FEATURES AND HARDWARE-SPECIFIC FEATURES

(71) Applicants: Jae-sun Seo, Tempe, AZ (US); Shihui Yin, Mesa, AZ (US); Sai Kiran Cherupally, Tempe, AZ (US)

(72) Inventors: Jae-sun Seo, Tempe, AZ (US); Shihui Yin, Mesa, AZ (US); Sai Kiran Cherupally, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 278 days.

(21) Appl. No.: 16/864,902

(22) Filed: May 1, 2020

(65) Prior Publication Data
US 2020/0349247 A1    Nov. 5, 2020

Related U.S. Application Data

(60) Provisional application No. 62/842,287, filed on May 2, 2019.

(51) Int. Cl.
*G06F 21/00* (2013.01)
*G06F 21/32* (2013.01)
(Continued)

(52) U.S. Cl.
CPC ............ *G06F 21/32* (2013.01); *A61B 5/0006* (2013.01); *G06N 3/08* (2013.01); *H04L 9/0866* (2013.01);
(Continued)

(58) Field of Classification Search
CPC ......... G06F 21/32; A61B 5/0006; G06N 3/08; H04L 9/0866; H04L 9/0869; H04L 9/3231; H04L 9/3278
(Continued)

(56) References Cited

U.S. PATENT DOCUMENTS 9,327,231 B2    5/2016 Lin et al.
9,466,362 B2    10/2016 Yu et al.
(Continued)

FOREIGN PATENT DOCUMENTS

WO    2020139895 A1    7/2020

OTHER PUBLICATIONS

Shihui Yin, Designing ECG-based Physical Unclonable Functionfor Security of Wearable Devices (Year: 2017).*
(Continued)

*Primary Examiner* — Andrew J Steinle
(74) *Attorney, Agent, or Firm* — Lewis Roca Rothgerber Christie LLP

(57) ABSTRACT

A smart hardware security engine using biometric features and hardware-specific features is provided. The smart security engine can combine one or more entropy sources, including individually distinguishable biometric features, and hardware-specific features to perform secret key generation for user registration and authentication. Such hybrid signatures may be distinct from person-to-person (e.g., due to the biometric features) and from device-to-device (e.g., due to the hardware-specific features) while varying over time. Thus, embodiments described herein can be used for personal device authentication as well as secret random key generation, significantly reducing the scope of an attack.

22 Claims, 12 Drawing Sheets

(51) Int. Cl.
  *H04L 9/32*   (2006.01)
  *H04L 9/08*   (2006.01)
  *A61B 5/00*   (2006.01)
  *G06N 3/08*   (2023.01)
(52) U.S. Cl.
  CPC .......... *H04L 9/0869* (2013.01); *H04L 9/3231* (2013.01); *H04L 9/3278* (2013.01)
(58) Field of Classification Search
  USPC ....................................................... 713/186
  See application file for complete search history.

(56) References Cited

U.S. PATENT DOCUMENTS

| | | | |
|---|---|---|---|
| 9,934,463 | B2 | 4/2018 | Seo et al. |
| 10,614,798 | B2 | 4/2020 | Seo et al. |
| 10,706,923 | B2 | 7/2020 | Seo et al. |
| 10,827,952 | B2 | 11/2020 | Yin et al. |
| 2015/0238140 | A1* | 8/2015 | LaBelle ............... A61B 5/0816 600/300 |
| 2017/0300815 | A1 | 10/2017 | Seo |
| 2018/0307912 | A1* | 10/2018 | Selinger ............... G06K 9/6256 |
| 2019/0087719 | A1 | 3/2019 | Seo et al. |
| 2019/0244100 | A1 | 8/2019 | Seo et al. |
| 2019/0354787 | A1* | 11/2019 | Fong ...................... G06N 3/084 |
| 2021/0082502 | A1 | 3/2021 | Seo et al. |

OTHER PUBLICATIONS

Muqing Liu, A Data Remanence based Approach to Generate 100% Stable Keys from an SRAM Physical Unclonable Function (Year: 2017).*

Alvarez et al.,"15fJ/b static physically unclonable functions for secure chip identification with <2% native bit instability and 140inter/intraPUF hamming distance separation in 65nm," 2015 IEEE International Solid-State Circuits Conference (ISSCC), Feb. 22-26, 2015, San Francisco, CA, pp. 256-257.

Alivecor, Inc., "Kardia Band by AliveCor: Instructions for use," 15LB1 Revision 3, Nov. 2016, 2 pages.

Biel et al., "ECG analysis: a new approach in human identification," IEEE Transactions on Instrumentation and Measurement ,vol. 50, No. 3, Jun. 2001, pp. 808-812.

Choi et al., "A PD control-based QRS detection algorithm for wearable ECG applications," 34th Annual Internation Conference of the IEEE EMBS, Aug. 28-Sep. 1, 2012, San Diego, CA, pp. 5638-5641.

Herder et al., "Physical unclonable functions and applications: a tutorial," Proceedings of the IEEE, vol. 102, No. 8, Aug. 2014, pp. 1126-1141.

Holcomb et al., "Power-up SRAM state as an identifying fingerprint and source of true random numbers," IEEE Transactions on Computers, vol. 58, No. 9, Sep. 2009, pp. 1198-1210.

Rhythm Technologies, Inc., "Zio by iRhythm. Proven to detect arrhythmias in one test for earlier diagnosis." Dec. 12, 2017, retrieved from internet: <https://web.archive.org/web/20171212181135/http://irhythmtech.com/products-services/about-zio>.

Israel et al., "ECG to identify individuals," Pattern Recognition, vol. 38, 2005, pp. 133-142.

Li et al., "A 562F2 Physically Unclonable Function with a Zero-Overhead Stabilization Scheme," 2019 IEEE International Solid-State Circuits Conference (ISSCC), Feb. 17-21, 2019, San Francisco, CA, 12 pages.

Li et al., "Ultra-compact and robust physically unclonable function based on voltage-compensated proportional-to-absolute-temperature voltage generators," IEEE Journal of Solid-State Circuits, vol. 51, No. 9, Sep. 2016, pp. 2192-2202.

Liu et al., "A data remanence based approach to generate 100% stable keys from an SRAM physical unclonable function," 2017 IEEE/ACM International Symposium on Low Power Electronics and Design (ISLPED), Jul. 24-26, 2017, Taipei, Taiwan, 6 pages.

Lourenço et al., "Outlier detection in non-intrusive ECG biometric system," International Conference Image Analysis and Recognition, Lecture Notes in Computer Science vol. 7950, 2013, pp. 43-52.

Mathew et al., "A 0.19 pJ/b PVT-variation-tolerant hybrid physically unclonable function circuit for 100% stable secure key generation in 22nm CMOS," 2014 IEEE Solid-State Circuits Conference, Feb. 11, 2014, pp. 278-279.

Page et al., "Utilizing deep neural nets for an embedded ECG-based biometric authentication system," 2015 IEEE Biomedical Circuits and Systems Conference (BioCAS), Oct. 22-4, 2015, Atlanta, GA, 4 pages.

Pan et al., "A real-time QRS detection algorithm," IEEE Transactiosn on Biomedical Engineering, vol. BME-32, No. 3, Mar. 1985, pp. 230-236.

Rukhin et al., "A statistical test suite for random and pseudorandom number generators for cryptographic applications," National Institute of Standards and Technology (NIST), Special Publication 800-22, Revision 1a, Apr. 2010, 131 pages.

Samsung Strategy & Innovation Center, "Samsung's Simband Open Reference Design Backgrounder," Mar. 26, 2017, retrieved from internet: <https://web.archive.org/web/20170326175223/http://www.samsung.com/us/ssic/pdf/Samsung_Simband_Backgrounder.pdf>; 3 pages.

Shen et al., "One-lead ECG for identity verification," Proceedings of the 2nd Joint Conference of the IEEE Engineering in Medicine and Biology Society and the BioMedical Engineering Society, Oct. 23-26, 2002, Houston, TX, pp. 62-63.

Suh et al., "Physical unclonable functions for device authentication and secret key generation," 44th ACM/IEEE Design Automation Conference, Jun. 4-8, 2007, San Diego, CA, pp. 9-14.

Venkatasubramanian et al., "PSKA: usable and secure key agreement scheme for body area networks," IEEE Transactions on Information Technology in Biomedicine, vol. 14, No. 1, Jan. 2010, pp. 60-68.

Yang et al., "A 23Mb/s 23pJ/b fully synthesized true-random-number generator in 28nm and 65nm CMOS," 2014 IEEE International Solid-State Circuits Conference, Feb. 11, 2014, pp. 280-281.

Yin et al., "A 1.06 µW smart ECG processor in 65 nm CMOS for real-time biometric authentication and personal cardiac monitoring," 2017 Symposium on VLSI Circuits Digest of Technical Papers, Jun. 5-8, 2017, Kyoto, Japan, 2 pages.

Yin et al., "Designing ECG-based physical unclonable function for security of wearable devices," 39th Annual International Conference of the IEEE Engineering in Medicine and Biology Society (EMBC), Jul. 11-15, 2017, Seogwipo, South Korea, pp. 3509-3512.

Zhang et al., "ECG-cryptography and authentication in body area networks," IEEE Transactions on Information Technology in Biomedicine, vol. 16, No. 6, Nov. 2012, pp. 1070-1078.

* cited by examiner

SMART HARDWARE SECURITY ENGINE USING BIOMETRIC FEATURES AND HARDWARE-SPECIFIC FEATURES

RELATED APPLICATIONS

This application claims the benefit of provisional patent application Ser. No. 62/842,287, filed May 2, 2019, the disclosure of which is hereby incorporated herein by reference in its entirety.

FIELD OF THE DISCLOSURE

This application relates to biometric authentication.

BACKGROUND

Traditional hardware designs for device authentication and secret key generation typically employ a physical unclonable function (PUF), which generates unique random numbers based on static random-access memory (SRAM), delay, or analog circuit elements. While silicon PUFs can be highly stable and unique, they do not represent liveness.

On the other hand, biometric authentication using fingerprint or iris for smartphones and Internet of Things (IoT) devices has become standardized, but effective spoofing attacks also have been reported. Physiological signals such as electrocardiograms (ECGs) provide liveness proof and have emerged as a new modality for authentication and secret key generation. The core challenge for ECG-based security is that ECG manifests in an identical way on multiple devices for a unique user, which exposes a larger attack surface and cannot be revoked once leaked.

SUMMARY

A smart hardware security engine using biometric features and hardware-specific features is provided. The smart security engine can combine one or more entropy sources, including individually distinguishable biometric features, and hardware-specific features to perform secret key generation for user registration and authentication. Such hybrid signatures may be distinct from person-to-person (e.g., due to the biometric features) and from device-to-device (e.g., due to the hardware-specific features) while varying over time. Thus, embodiments described herein can be used for personal device authentication as well as secret random key generation, significantly reducing the scope of an attack.

A smart wearable hardware security engine according to embodiments disclosed herein may combine multiple different sources of entropy, such as electrocardiogram (ECG), heart rate variability (HRV), and a static random-access memory (SRAM)-based physical unclonable function (PUF), to perform real-time authentication and generate unique and random signatures. A prototype chip fabricated in 65 nanometer (nm) low power (LP) complementary metal oxide semiconductor (CMOS) consumes 8.013 microwatts ($\mu W$) at 0.6 volts (V) for real-time authentication. Compared to ECG-only authentication, the equal error rate of multi-source authentication is reduced by ~8× down to 0.09% for a 741-subject in-house database. In addition, the effectiveness of combining multiple entropy sources for random secret key generation is evaluated using National Institute of Standards and Technology (NIST) randomness tests, by analyzing various trade-offs and optimizations in aggregating ECG and HRV features with SRAM PUF values.

An exemplary embodiment provides a method for biometric authentication. The method includes generating a biometric feature vector from biometric data, the biometric feature vector identifying a user; generating a hardware-specific feature vector; and generating a secret key based on the biometric feature vector and the hardware-specific feature vector.

Another exemplary embodiment provides a circuit. The circuit includes hardware-specific feature circuitry capable of producing a hardware-specific feature vector and a processor. The processor is configured to receive a biometric signal; extract a biometric feature vector from the biometric signal, the biometric feature vector identifying a user; receive the hardware-specific feature vector from the hardware-specific feature circuitry; and generate a secret key based on the biometric feature vector and the hardware-specific feature vector from the hardware-specific feature circuitry.

Another exemplary embodiment provides a device. The device includes a memory and a processor coupled to the memory. The processor is configured to: receive biometric data; extract a biometric feature vector unique to a user from the biometric data; generate a hardware-specific feature vector; and authenticate the user based on the biometric feature vector and the hardware-specific feature vector.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1:
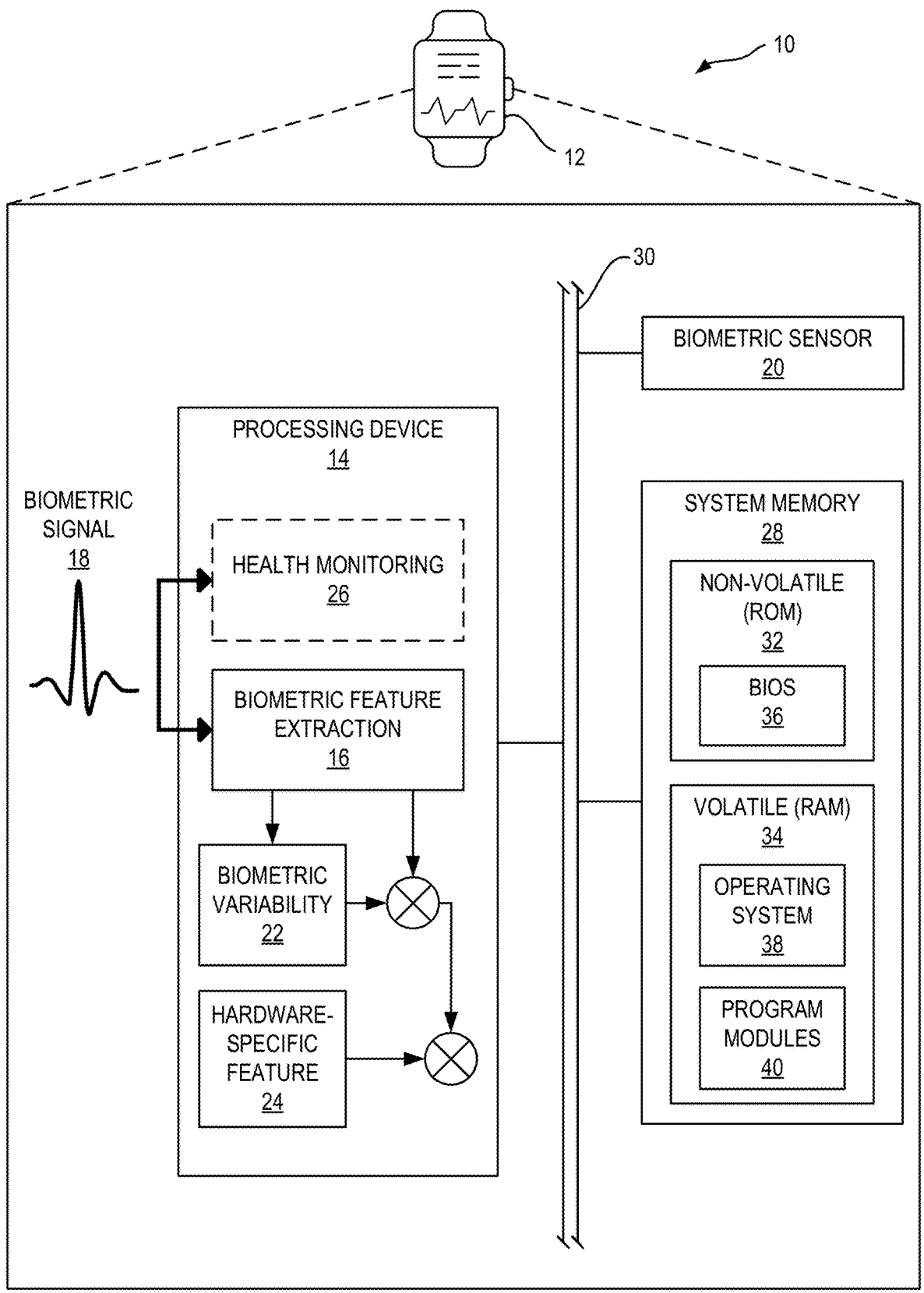
FIG. 1 is a schematic diagram of a smart hardware security engine according to embodiments described herein.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

A smart hardware security engine using biometric features and hardware-specific features is provided. The smart security engine can combine one or more entropy sources, including individually distinguishable biometric features, and hardware-specific features to perform secret key generation for user registration and authentication. Such hybrid signatures may be distinct from person-to-person (e.g., due to the biometric features) and from device-to-device (e.g., due to the hardware-specific features) while varying over time. Thus, embodiments described herein can be used for personal device authentication as well as secret random key generation, significantly reducing the scope of an attack.

A smart wearable hardware security engine according to embodiments disclosed herein may combine multiple different sources of entropy, such as electrocardiogram (ECG), heart rate variability (HRV), and a static random-access memory (SRAM)-based physical unclonable function (PUF), to perform real-time authentication and generate unique and random signatures. A prototype chip fabricated in 65 nanometer (nm) low power (LP) complementary metal oxide semiconductor (CMOS) consumes 8.013 microwatts ($\mu$W) at 0.6 volts (V) for real-time authentication. Compared to ECG-only authentication, the equal error rate of multi-source authentication is reduced by ~8× down to 0.09% for a 741-subject in-house database. In addition, the effectiveness of combining multiple entropy sources for random secret key generation is evaluated using National Institute of Standards and Technology (NIST) randomness tests, by analyzing various trade-offs and optimizations in aggregating ECG and HRV features with SRAM PUF values.

The approach described herein has three key advantages. First, combining the entropies from multiple independent sources enables an efficient multi-factor authentication where both possession of the hardware (e.g., silicon asset) and biometric match is accounted for simultaneously in the authentication process. Second, using multiple sources of entropy guarantees that biometric information is never used in its raw form. Hence, the scope of an attack is significantly reduced by making it imperative for an attacker to know both the hardware-specific features (e.g., silicon PUF) as well as the biometric (e.g., ECG/HRV) features to uncover the root of trust. The hardware-specific features (e.g., a unique silicon PUF) will provide different IDs on different devices, and the same chip can be configured to authenticate multiple users due to their own unique IDs owing to unique biometric (e.g., ECG/HRV) features. Third, authentication can still be performed when one or two of these entropy sources are compromised (or fail to function as expected).

In this regard, a new physiological signal feature extraction framework, application-specific neural network training algorithm, and custom hardware design are explored.

Employing the cost function directly driven by feature distribution, the performance of authentication and secret key generation is significantly improved.

For biometric features (e.g., cardiac features from an ECG sensor, a photoplethysmography (PPG) sensor, or another cardiac sensor), the neural network can be trained with an application-specific cost function at the last hidden layer, based on the intra-subject and inter-subject cosine similarity distributions. The neural network will optimize and suppress the equal error rate (EER) for misclassifying inter-subject as intra-subject and vice versa. Overall, by evaluating Hamming distance between registered and newly extracted features, secure access can be granted.

Ideally, the intra-subject Hamming distance should be very close to zero with a tight distribution. However, due to the time-variant nature of physiological signals, a subject's ECG, HRV, PPG, and gait signals could vary noticeably from time to time. Such variability can be exploited, where each variability source can contribute to the enhanced randomness of the final feature vector. For example, if an XOR function is applied to ECG-only features and HRV features, the preliminary results show that the randomness substantially improves to make the percentage of 1s and 0s in the XORed feature vector to be tightly distributed around 50%.

I. Hardware Security Engine Design

FIG. 1 is a schematic block diagram of a smart hardware security engine 10 according to embodiments described herein. The smart hardware security engine 10 includes or is implemented as a wearable device 12, a mobile device, or other computer system which comprises any computing or electronic device capable of including firmware, hardware, and/or executing software instructions that could be used to perform any of the methods or functions described herein, such as biometric authentication. In this regard, the smart hardware security engine 10 may be a circuit or circuits included in an electronic board card, such as a printed circuit board (PCB), a server, a personal computer, a desktop computer, a laptop computer, an array of computers, a personal digital assistant (PDA), a computing pad, a mobile device, a wearable device, or any other device, and may represent, for example, a user's electronic device.

The smart hardware security engine 10 of the present disclosure can perform two main tasks: secure authentication and random secret key generation. For both tasks, one or more biometric feature vectors are generated from biometric data of a user, and a hardware-specific feature vector is generated by circuitry in the smart hardware security engine 10. The biometric feature vector(s) and the hardware-specific feature vector are combined to generate a random number, which may be a secret key for authentication or other security purposes (e.g., use as an encryption key or for generating an encryption key).

In this regard, the smart hardware security engine 10 includes a processing device 14 or processor configured to execute processing logic instructions for performing the operations and steps discussed herein, including biometric feature extraction 16 and user authentication or other security features. The processing device 14 represents one or more commercially available or proprietary general-purpose processing devices, such as a microprocessor, central processing unit (CPU), or the like. More particularly, the processing device 14 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets.

In this regard, various illustrative logical blocks, modules, and circuits described in connection with the embodiments disclosed herein may be implemented or performed with the processing device 14, which may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 14 may be a microprocessor, or may be any conventional processor, controller, microcontroller, or state machine. The processing device 14 may also be implemented as a combination of computing devices (e.g., a combination of a DSP and a microprocessor, a plurality of microprocessors, one or more microprocessors in conjunction with a DSP core, or any other such configuration).

In an exemplary aspect, the processing device 14 performs biometric feature extraction 16 on one or more biometric signals 18 (which may be received from one or more biometric sensors 20). After biometric feature extraction 16, a biometric feature vector can be combined (e.g., using bit-wise XOR) with another biometric entropy source (from a biometric variability function 22) and a hardware-specific feature vector (from a hardware-specific feature function 24) to generate the secret key for authentication or other security purposes. In some examples, the processing device 14 may concurrently perform other functions, such as an optional health monitoring function 26 with the biometric signals 18.

The smart hardware security engine 10 further includes a system memory 28, and a system bus 30. The system memory 28 may include non-volatile memory 32 and volatile memory 34. The non-volatile memory 32 may include read-only memory (ROM), erasable programmable read-only memory (EPROM), electrically erasable programmable read-only memory (EEPROM), and the like. The volatile memory 34 generally includes random-access memory (RAM) (e.g., static random-access memory (SRAM) and dynamic random access memory (DRAM), such as synchronous DRAM (SDRAM)). A basic input/output system (BIOS) 36 may be stored in the non-volatile memory 32 and can include the basic routines that help to transfer information between elements within the smart hardware security engine 10.

The system bus 30 provides an interface for system components including, but not limited to, the system memory 28 and the processing device 14. The system bus 30 may be any of several types of bus structures that may further interconnect to a memory bus (with or without a memory controller), a peripheral bus, and/or a local bus using any of a variety of commercially available bus architectures.

An operating system 38 and any number of program modules 40 or other applications can be stored in the volatile memory 34, wherein the program modules 40 represent a wide array of computer-executable instructions corresponding to programs, applications, functions, and the like that may implement the functionality described herein in whole or in part, such as through instructions on the processing device 14. The program modules 40 may also reside on a storage mechanism provided by another storage device. As such, all or a portion of the functionality described herein may be implemented as a computer program product stored on a transitory or non-transitory computer-usable or computer-readable storage medium, such as the storage device, volatile memory 34, non-volatile memory 32, instructions on the processing device 14, and the like. The computer program product includes complex programming instructions, such as complex computer-readable program code, to cause the processing device 14 to carry out the steps necessary to implement the functions described herein.

The biometric sensor 20 may provide one or more biometric signals 18 indicating a live biometric state (e.g., heart rate, heart waveform, respiratory rate, respiratory waveform, retinal response, gait, voice, conductance/resistivity of a user, etc.) of a user to provide one or more entropy sources for user authentication. The biometric sensor 20 is also coupled to the processing device 14 and the system memory 28 via the system bus 30. Additional inputs and outputs to the smart hardware security engine 10 and/or the wearable device 12 may be provided through the system bus 30 as appropriate to implement embodiments described herein.

Figure 2:
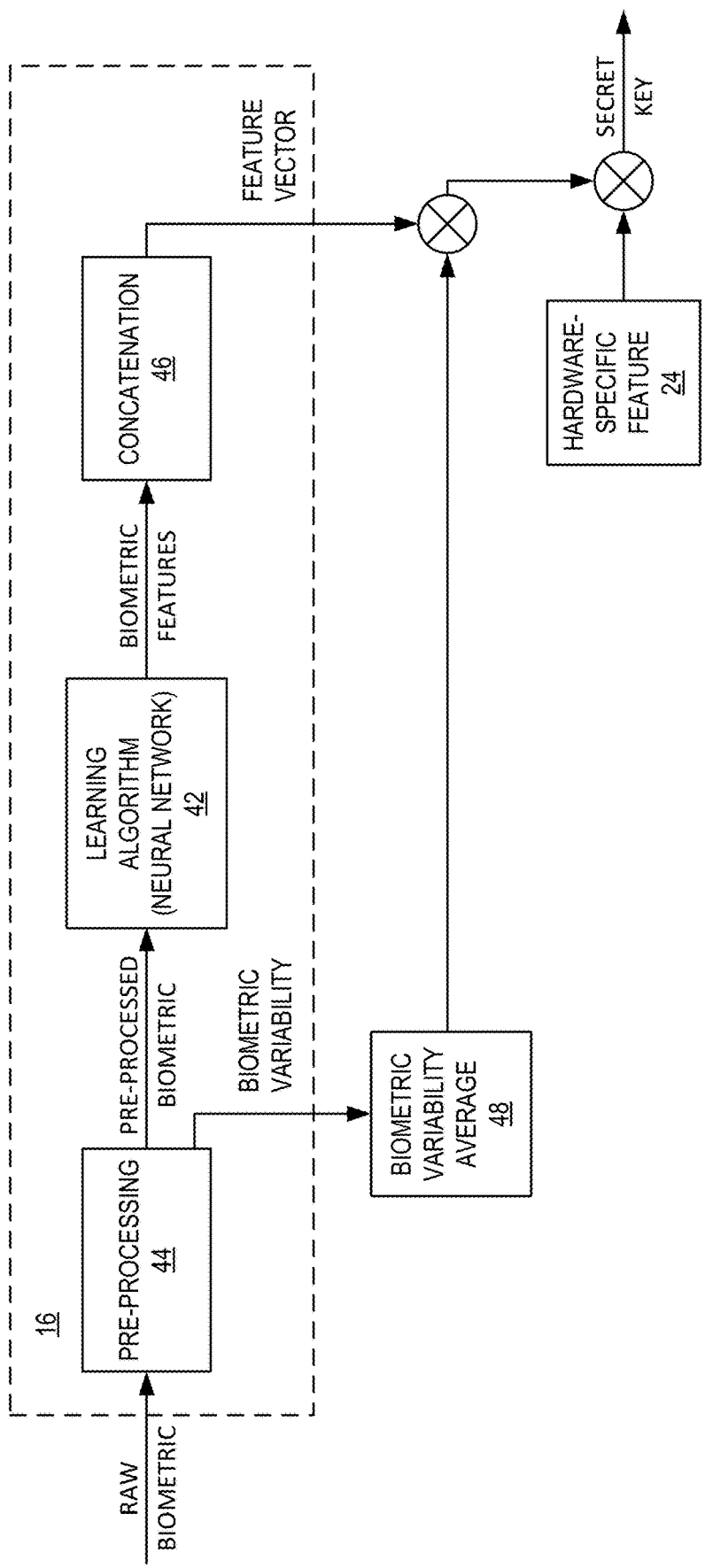
FIG. 2 is a flow diagram of an overview of a process for biometric authentication performed by the smart hardware security engine of FIG. 1, which includes biometric feature extraction using a learning algorithm.

FIG. 2 is a flow diagram of an overview of a process for biometric authentication performed by the smart hardware security engine 10 of FIG. 1, which includes biometric feature extraction 16 using a learning algorithm. In an exemplary aspect, raw biometric data (e.g., the biometric signal 18 of FIG. 1) is pre-processed before applying a learning algorithm 42. At a pre-processing stage 44, the raw biometric data can be filtered, periodic features can be identified and tracked, outlier data can be suppressed, and so on to improve performance of the learning algorithm 42.

The pre-processing stage 44 provides pre-processed biometric data as an input to the learning algorithm 42, which may be operated on a neural network. Generally, the learning algorithm 42 is pre-trained to distinguish between biometric signals of different users. Thus, the biometric features produced by the learning algorithm 42 are used to generate a randomized number unique to a particular user. At a concatenation stage 46, the biometric features produced by the learning algorithm 42 are concatenated into a biometric feature vector.

Figure 3:
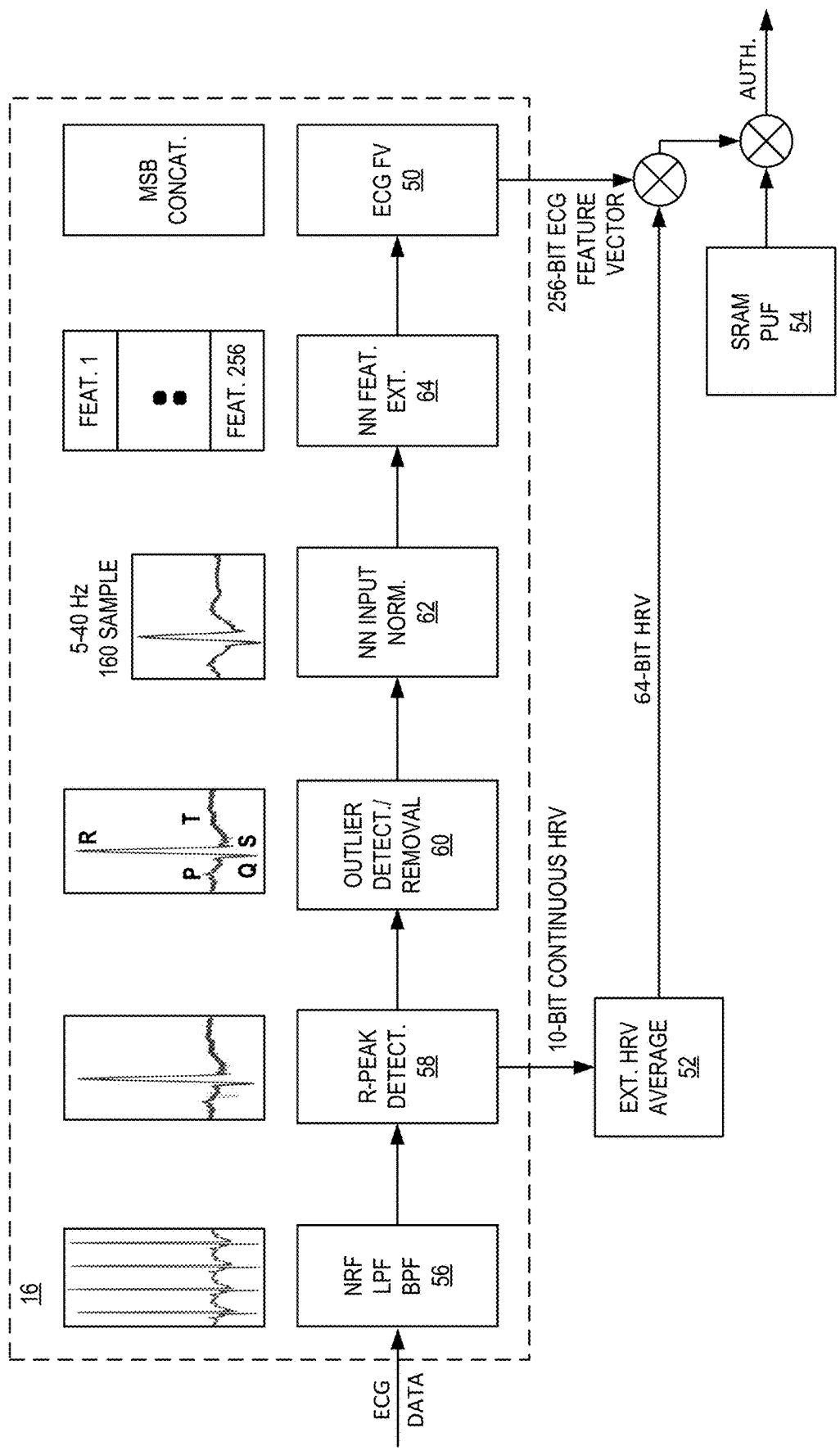
FIG. 3 is a flow diagram illustrating in further detail an example of the process of FIG. 2 using raw electrocardiogram (ECG) data and a pre-trained neural network to extract ECG features.

The pre-processing stage 44 may further provide biometric variability data for an additional entropy source for the biometric authentication process. The biometric variability data can be averaged 48 before being combined with the biometric feature vector from the biometric feature extraction 16 and a hardware-specific feature vector produced by the hardware-specific feature function 24. This generates a randomized secret key that is user-specific, hardware-specific, and robust to falsification (e.g., spoofing). Details of an example pre-processing stage 44 and neural network applying the learning algorithm 42 are described further below A. Pre-Processing and Neural Network FIG. 3 is a flow diagram illustrating in further detail an example of the process of FIG. 2 using raw ECG data and a pre-trained neural network to extract ECG features. In the example illustrated in FIG. 3, the biometric feature extraction 16 receives ECG data (e.g., an ECG signal from an ECG sensor; alternatively, a cardiac signal from a PPG sensor), and extracts a 256-bit ECG feature vector 50 and a 64-bit average HRV value 52. The 256-bit ECG feature vector 50, average HRV value 52, and an SRAM-based PUF 54 (e.g., from 64-bit to 256-bit) are combined using bitwise XOR to generate a 256-bit random number. The variations in ECG patterns obtained from different subjects, heart rates over time, and SRAM power-on states of different chips enables the resultant bit-vector to be used as a randomized secret key for registering a user, authenticating a registered user, generating an encryption key, and other security functions.

In an exemplary aspect, the process for biometric feature extraction 16 includes pre-processing steps, such as applying a finite impulse response (FIR) filter 56 (which can include one or more of a noise reduction filter (NIF), a low pass filter (LPF), and/or a Berkeley packet filter (BPF)). Additional pre-processing steps include R-peak detection 58, detection and removal of outlier data 60, and normalizing the ECG data to the neural network input 62. Finally, the neural network extracts ECG features 64, which are concatenated to produce the 256-bit ECG feature vector 50.

Figure 4:
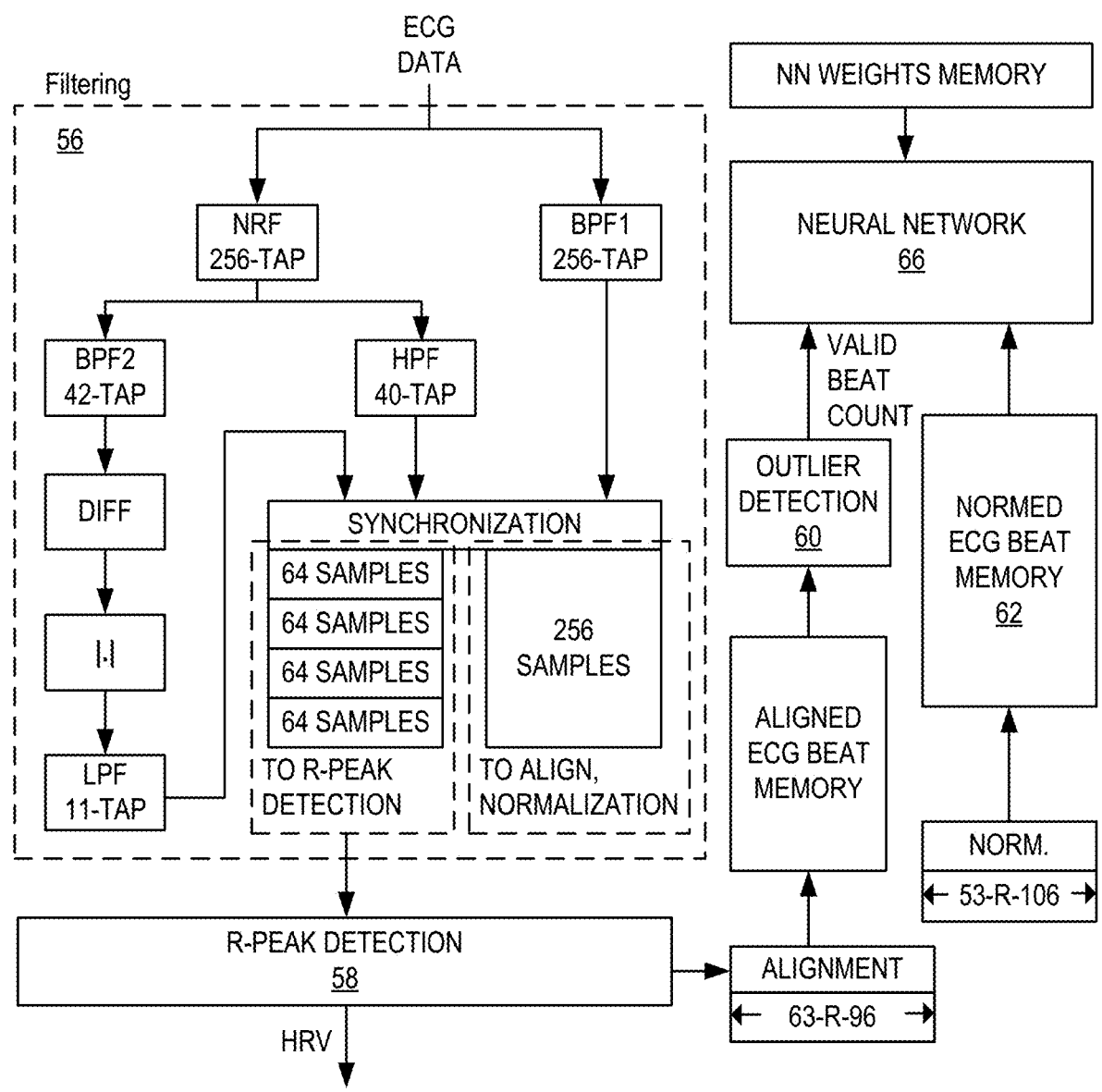
FIG. 4 is a schematic diagram illustrating a pre-processing flow for the ECG data in accordance with an example of the process of FIG. 3.

FIG. 4 is a schematic diagram illustrating a pre-processing flow for the ECG data in accordance with an example of the process of FIG. 3. Raw digitized ECG data goes through stages of FIR filtering 56, R-peak detection 58, alignment, and normalization 62. The ECG pre-processing flow uses only two BPFs (a 2× reduction over traditional approaches) and the memory size used for alignment and normalization is reduced by 4×.

The ECG beats are aligned around the R-peak by having 63/96 samples before/after the R-peak. After this, the extracted ECG beats are passed through the outlier detector/remover module 60 and the normalization module 62. The outlier-free ECG beats are fed to a neural network 66, an example of which is further described with respect to FIG. 5.

Figure 5:
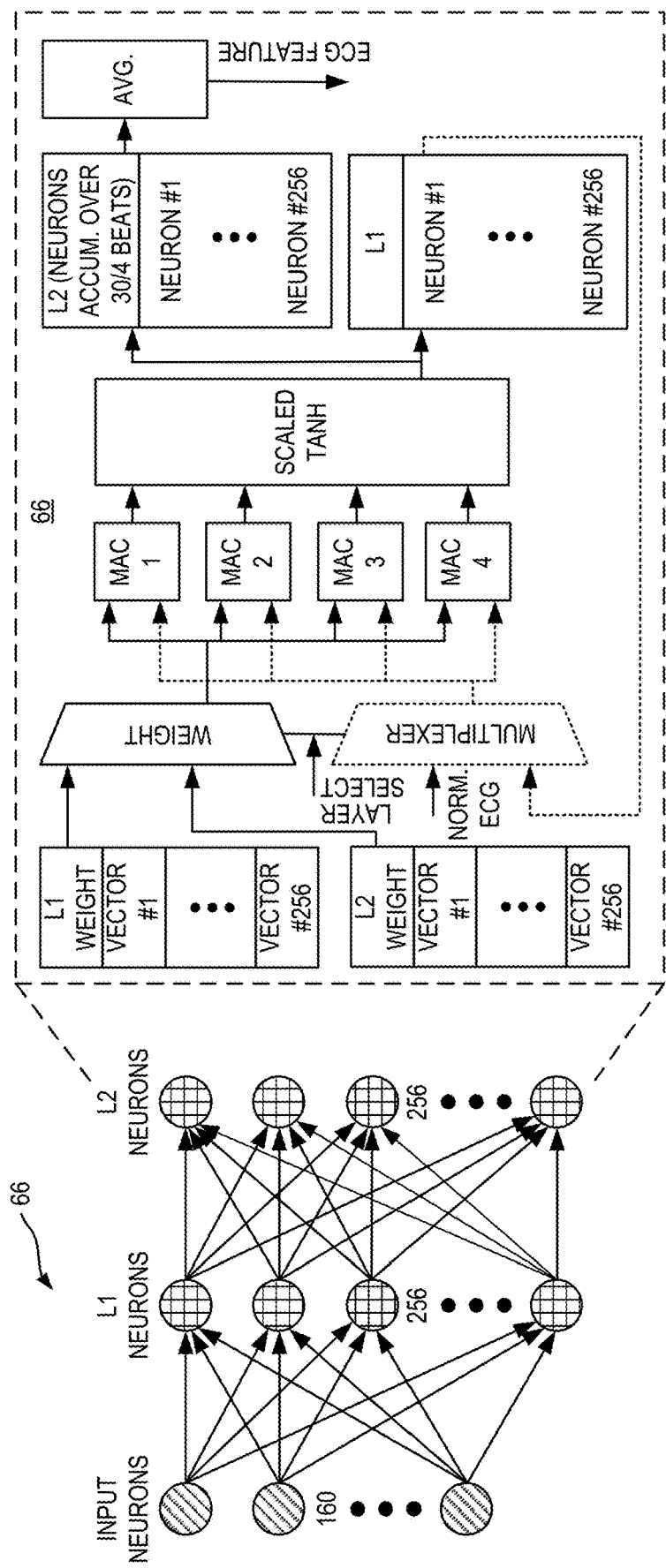
FIG. 5 is a schematic diagram illustrating an exemplary neural network having an input layer and two hidden layers applying the learning algorithm of FIG. 3 for biometric feature extraction.

FIG. 5 is a schematic diagram illustrating an exemplary neural network 66 having an input layer and two hidden layers applying the learning algorithm 42 of FIG. 3 for biometric feature extraction. In some examples, the neural network 66 is a single fully connected neural network with 160 input neurons and two hidden layers containing 256 neurons per layer. The neural network can be trained to maximize the separation between intra-subject distribution and inter-subject distribution and therefore to minimize the EER, as discussed further below.

In the illustrated embodiment, blocks L1 Weight and L2 Weight are spatially aligned memory arrays (e.g., sharing the same row address) arranged such that when the same row is read from all the memory arrays, it corresponds to the weights of the connections of one hidden layer neuron. For example, row 1 from L1 Weight corresponds to 160 weights of the 160 connections to neuron 1 in hidden layer 1 (because there are 160 neurons in the preceding layer (input layer)). Row 1 from L2 Weight corresponds to 256 weights of the 256 connections to neuron 1 in hidden layer 2. Up to four rows of weights are read per clock cycle, and multiplexers are used to select between the inputs to the first hidden layer or the second hidden layer. Four individual processing elements (PEs) (e.g., applying multiply accumulate operation (MAC) 1, MAC 2, MAC 3, MAC 4) are used to evaluate the dot products of the weights and inputs corresponding to four hidden layer neurons in one clock cycle. These are then processed through a scaled tan h activation function to obtain the hidden neuron outputs. These outputs are then stored in buffers L1 and L2. L2 buffer has accumulators for accumulating the second hidden layer neuron outputs which are obtained across 30 or 4 ECG beats. Finally, the second hidden layer neuron outputs are averaged and then the ECG feature vector is formed.

In this regard, 256 ECG features are extracted from the output of the second hidden layer, and the smart hardware security engine 10 can be configured to extract features from averaging over a number of consecutive ECG heart beats of the subject (e.g., 30 beats for more stable extraction, 4 beats for faster feature extraction). In some examples, when registering a user the smart hardware security engine 10 can be configured to extract features from averaging over a greater number of heart beats (e.g., as few as 8, but preferably 30 or more heart beats) and authentication can be performed from averaging over a lesser number of heart beats (e.g., generally between 4 and 8 heart beats, up to the number used during registration). The features extracted from each beat are accumulated in internal registers and averaged over the number of valid beats processed for each subject. Finally, each user's representative 256-bit ECG feature vector is obtained by taking the most significant bits (MSBs) from these average values of 256 features.

It should be understood that the neural network 66 of FIG. 5 is exemplary in nature, and other examples may be implemented differently (e.g., with more or fewer layers, with more or fewer bits per layer). In some examples, one or more of the hidden layers may be sparsely connected layers, which may lower memory requirements and potentially lower latency at some cost to accuracy (e.g., EER).

B. Neural Network Training

Multi-layer neural networks, such as the neural network 66 of FIG. 5, can learn representative features at one or more hidden layer(s) and classify or regress based on the extracted features at an output layer. Conventional neural network training employs one-hot coding output labels, where only one output neuron corresponding to the input data is given "+1" label and other output neurons are given "0" labels. Using a neural network trained with one-hot coding labels, authentication can be performed using the extracted features at the last hidden layer, instead of the output layer. For example, by evaluating the cosine similarity between the newly extracted features and registered features, secure data access can be granted if the similarity is above a certain threshold. Cosine similarity between two feature vectors $FV_1$ and $FV_2$ is defined as:

$$sim_{cos} = \frac{FV_1 \cdot FV_2}{\|FV_1\|_2 \|FV_2\|_2}$$

Cosine distance (CD) between $FV_1$ and $FV_2$ is defined as:

$$d_{cos} = 1 - sim_{cos}$$

To have good authentication accuracy, the overlap between the intra-subject CD and inter-subject CD should be minimized. The commonly-used one-hot labels are not necessarily best suited for this purpose, because when the neural network is trained with one-hot labels, the neural network is not aware of how the extracted features at the hidden layers will be used. In other words, the neural network trained with one-hot labels produces good features for classification at the output layer, but may not be most suitable for authentication based on CD between features at the hidden layer.

Therefore, some embodiments train the neural network 66 without the output layer and one-hot labels, but with an application-specific cost function at the last hidden layer. In particular, the application-specific cost function can be formulated as:

$$\text{cost} = -\frac{\mu_{intra} - \mu_{inter}}{\sigma_{intra} + \sigma_{inter}}$$

wherein $\mu_{intra}$ and $\mu_{inter}$ are the mean of the intra-subject and inter-subject cosine similarity distributions, respectively, and $\sigma_{intra}$ and $\sigma_{inter}$ are the standard deviation of the intra-subject and inter-subject cosine similarity distributions, respectively.

If inter-/intra-subject cosine similarities follow normal distributions $\mathcal{N}(\mu_{inter}, \sigma_{inter}^2)$ and $\mathcal{N}(\mu_{intra}, \sigma_{intra}^2)$, and if the threshold is set at $$\theta = \frac{\mu_{inter}\sigma_{intra} + \mu_{intra}\sigma_{inter}}{\sigma_{inter} + \sigma_{intra}},$$

then the EER can be derived for misclassifying inter-subject as intra-subject and for misclassifying intra-subject as inter-subject. The relative distances of $\theta$ from $\mu_{inter}$ in terms of $\sigma_{inter}$ and from $\mu_{intra}$ in terms of $\sigma_{intra}$ are both equal to $$\frac{\mu_{intra} - \mu_{inter}}{\sigma_{inter} + \sigma_{intra}}.$$

Larger relative distance will result in smaller EER. Thus, by minimizing the cost function, the relative distance is maximized and the EER is minimized.

The neural network 66 of FIG. 5 (with 2 hidden layers and 256 neurons per each layer) is trained. The activation function is tan h. Back propagation with stochastic gradient descent learning is adopted to train the network. During training, $\mu_{inter}$, $\mu_{intra}$, $\sigma_{inter}$ and $\sigma_{intra}$ are estimated for each single batch. To have good estimations, a large batch size of 3,000 is used to contain sufficiently large number of pairs of interclass examples and intra-class examples. Dropout is employed at the first hidden layer with dropout ratio of 0.2.

C. Heart Rate Variability and SRAM PUF

In addition to the ECG features, in some embodiments the biometric feature extraction 16 also produces a continuous 10-bit HRV value. The HRV is a measure of variation in instantaneous heart rates, which is the inverse of the time interval between successive R-R peaks. These HRV values are collected for the duration of the ECG data for each subject and averaged externally (e.g., the average HRV value 52) to obtain a 64-bit HRV value using floating point arithmetic. In some examples, the averaged HRVs are bit-wise XORed with bits [143:112] and [79:48] (or other bits) of the 256-bit ECG feature vector to enhance randomness.

For SRAM-based PUF generation, a 512-bit on-chip SRAM is integrated in a prototype chip (discussed further below with respect to FIG. 9). In addition, an off-the-shelf SRAM chip was used to generate one 256-bit PUF vector from each 8K×8-bit SRAM memory block, using a data remanence approach. In total, four 32K×8-bit off-the-shelf SRAM chips were used to generate 16 stable PUF vectors, as shown in FIG. 6.

Figure 6:
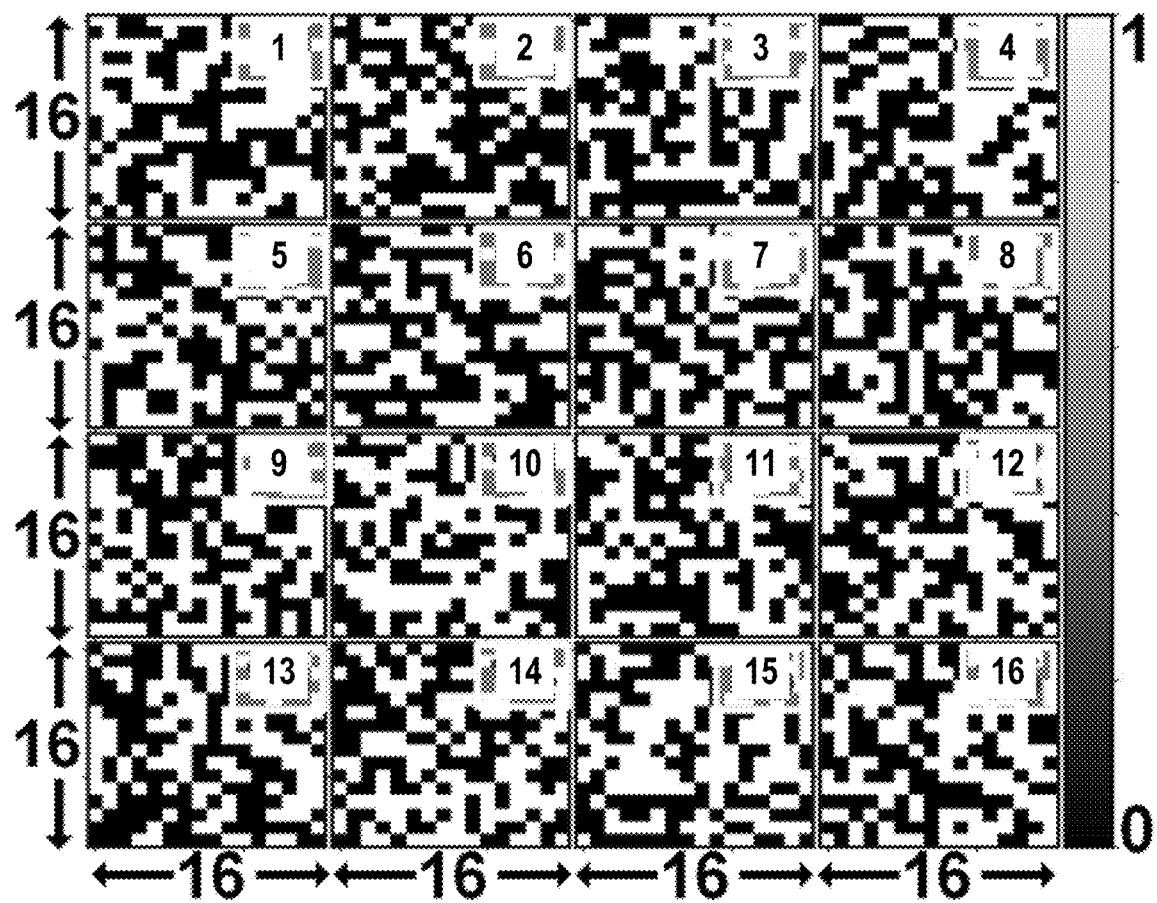
FIG. 6 is a graphical diagram illustrating the stability of sixteen 256-bit physical unclonable functions (PUFs), where each 256-bit PUF is represented as a 16×16 matrix.

FIG. 6 is a graphical diagram illustrating the stability of sixteen 256-bit PUFs, where each 256-bit PUF is represented as a 16×16 matrix. Each cell represents the normalized sum of each bit's value across 40 power-on instances performed at random intervals ranging between 500 ms to 5 minutes. Sixteen 256-bit PUF vectors (or smaller number of bits) are bitwise XORed with 16 256-bit ECG feature vectors of 16 randomly picked subjects from the database. The optimal remanence period was found to be between 60 ms and 100 ms for the four chips, which resulted in selection of 100% stable cells that are either strongly biased towards '0' or '1', all passing the NIST randomness tests.

D. Performance and Design Optimization

The EER obtained from the inter-class and intra-class Hamming distance distributions for an in-house 741-subject database is used in experimental embodiments as the optimization metric. Parameters such as SRAM PUF length, HRV bit-width, weight, and activation precision of the neural networks were optimized through experimentation. The output of the second hidden layer is used to obtain the ECG feature vector, and hence an output layer is not needed. In an exemplary aspect, the MSBs of the mean outputs of the second hidden layer neurons are accumulated across several beats to form the 256-bit feature vector.

Figure 7:
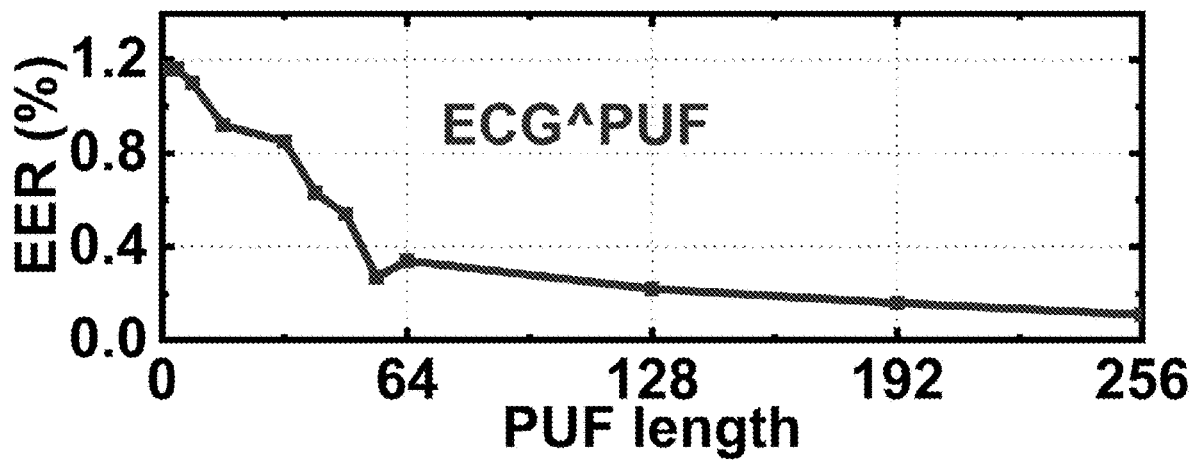
FIG. 7 is a graphical representation of the equal error rate (EER) of a static random-access memory (SRAM)-based PUF as a function of PUF length.

FIG. 7 is a graphical representation of the EER of a SRAM-based PUF as a function of PUF length. For the ECG⊕PUF scheme, EER decreased from 0.9% to 0.336% to 0.11% when the SRAM PUF vector size is increased from 32-bit to 64-bit to 256-bit.

Figure 8:
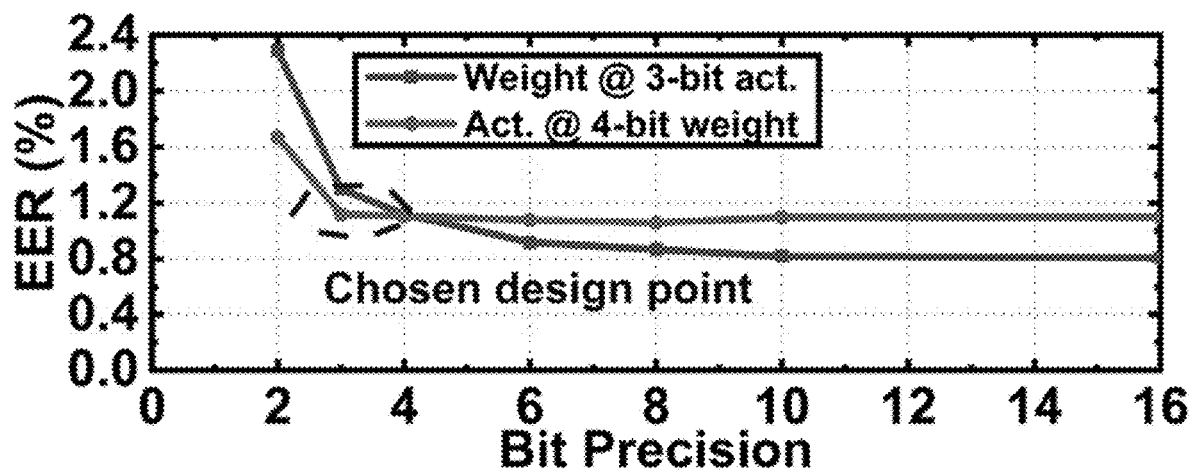
FIG. 8 is a graphical representation illustrating a trade-off of EER as the precision and memory requirement of the neural network is reduced.

FIG. 8 is a graphical representation illustrating a trade-off of EER as the precision and memory requirement of the neural network is reduced. The power and area were optimized by using a low-precision neural network and time-multiplexed operation. 0.3% EER was traded off for reducing the neural network precision to 3-bit activation and 4-bit weights, substantially reducing the neural network area and computation. In addition, clock-gated and time-multiplexed data paths are used to optimize the latency and throughput of arithmetic functions such as computing mean, variance, inverse square root, and weighted sum over time. The precision of FIR filtering, R-peak detection, outlier detection, and normalization were reduced to 13-b, 13-b, 11-b and 12-b, respectively, with minimal accuracy degradation compared to software simulations.

II. Measurement Results

Figure 9:
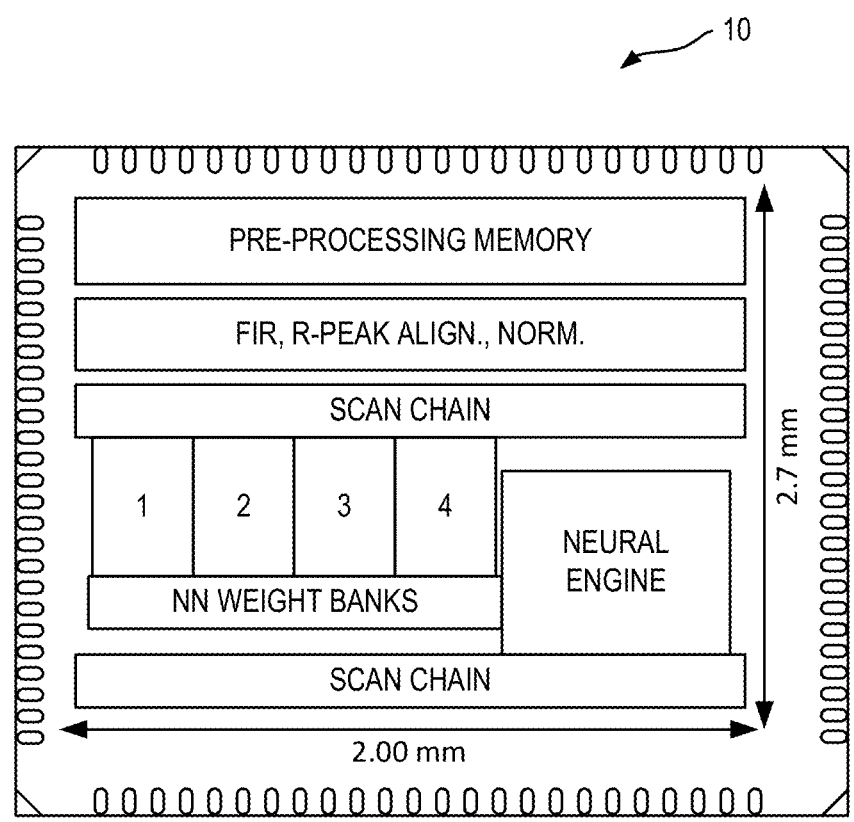
FIG. 9 illustrates a micrograph of a 65 nm prototype chip for the smart hardware security engine of FIG. 1.

FIG. 9 illustrates a micrograph of a 65 nm prototype chip for the smart hardware security engine 10 of FIG. 1. The prototype chip was implemented in 65 nm LP CMOS. The total on-chip memory is 64 kB, where 52 kB is used for neural network weights. The chip occupies a total area of 7.54 mm$^2$ with 98 digital I/O pads for external communication. In this and other embodiments, the hardware-specific features are generated by a SRAM-based PUF. In some examples, the hardware implementation of neural networks on the smart hardware security engine 10 will employ SRAMs. Therefore, rather than employing an additional SRAM for the purpose of PUF, the neural network SRAM can be used to generate the PUF. In such a silicon PUF, typically the post-processing module consists of dark-bit masking, error correction, fuzzy extraction, etc., which are computation heavy.

Due to the limited number of SRAM PUF vectors (16) available that governs the number of unique SRAM PUF responses, 16 subjects were randomly picked from the in-house 741-subject database and processed using the security engine of the present disclosure. For accurate results, 30 beats per subject were averaged to obtain one feature vector. Four different starting points were used per subject to evaluate the time variance in the raw ECG waveforms. As shown in FIGS. 10A-10C and FIGS. 11A-11C, EER values of 1.12%, 0.11%, and 0.09% are achieved for ECG-only, ECG⊕PUF, and ECG⊕PUF⊕HRV schemes, respectively.

Figure 10A:
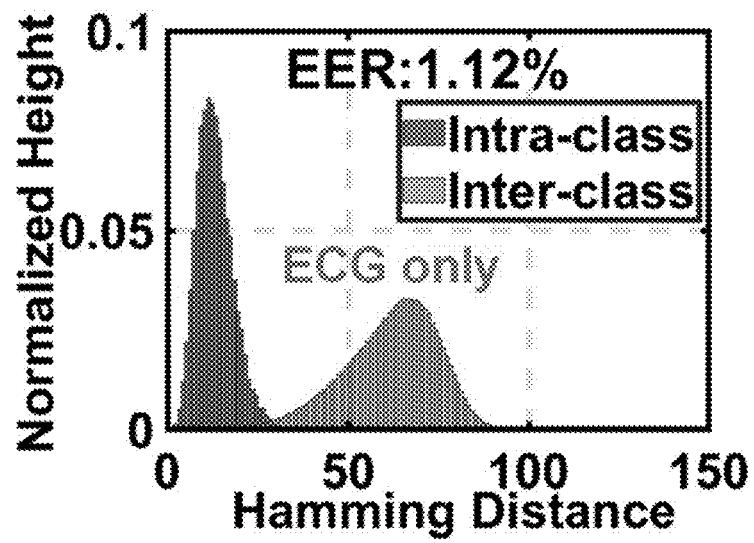
FIG. 10A is a graphical representation of EER between inter-class and intra-class Hamming distance distributions for ECG feature vector extraction only.
Figure 10B:
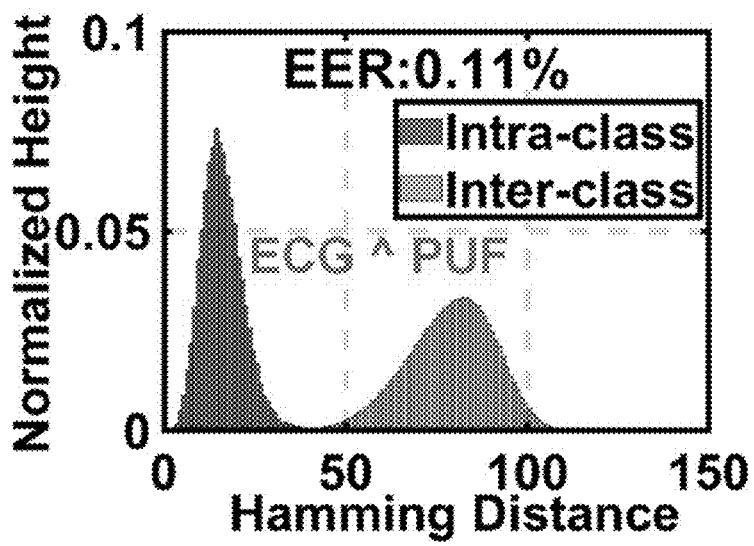
FIG. 10B is a graphical representation of EER between inter-class and intra-class Hamming distance distributions for ECG feature vector extraction combined with the PUF vector.
Figure 10C:
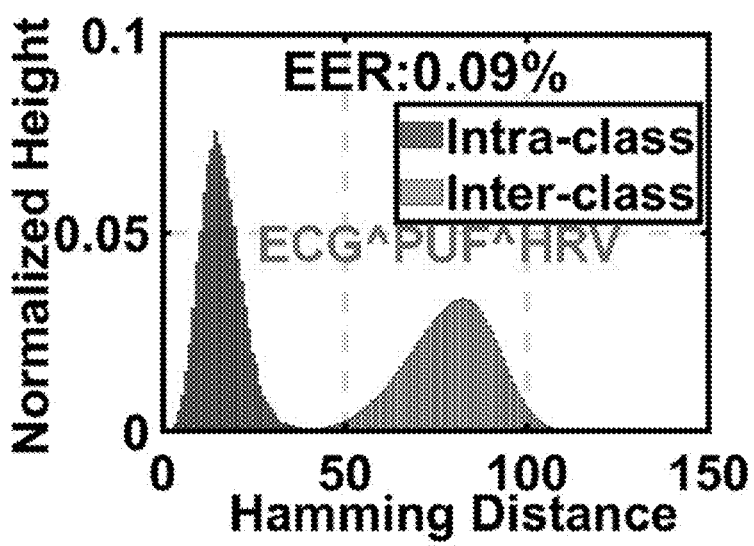
FIG. 10C is a graphical representation of EER between inter-class and intra-class Hamming distance distributions for ECG feature vector extraction combined with the PUF vector and heart rate variability (HRV).

FIG. 10A is a graphical representation of EER between inter-class and intra-class Hamming distance distributions for ECG feature vector extraction only. FIG. 10B is a graphical representation of EER between inter-class and intra-class Hamming distance distributions for ECG feature vector extraction combined with the PUF vector. FIG. 10C is a graphical representation of EER between inter-class and intra-class Hamming distance distributions for ECG feature vector extraction combined with the PUF vector and HRV.

Figure 11A:
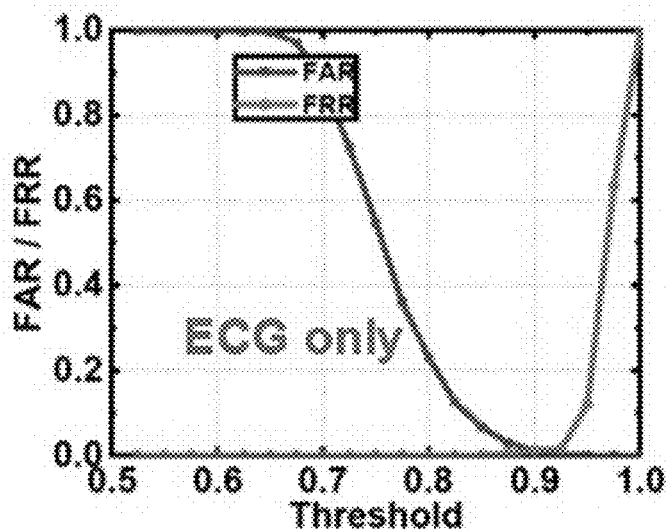
FIG. 11A is a graphical representation of a false acceptance rate (FAR)-false rejection rate (FRR) plot corresponding to the Hamming distance distribution of FIG. 10A.
Figure 11B:
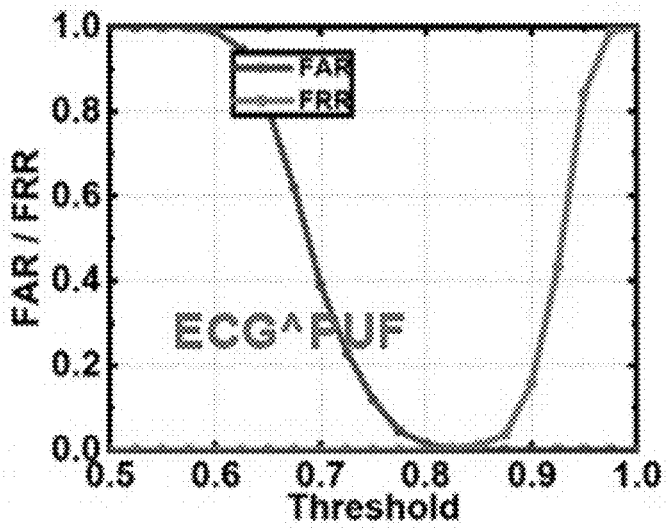
FIG. 11B is a graphical representation of a FAR-FRR plot corresponding to the Hamming distance distribution of FIG. 10B.
Figure 11C:
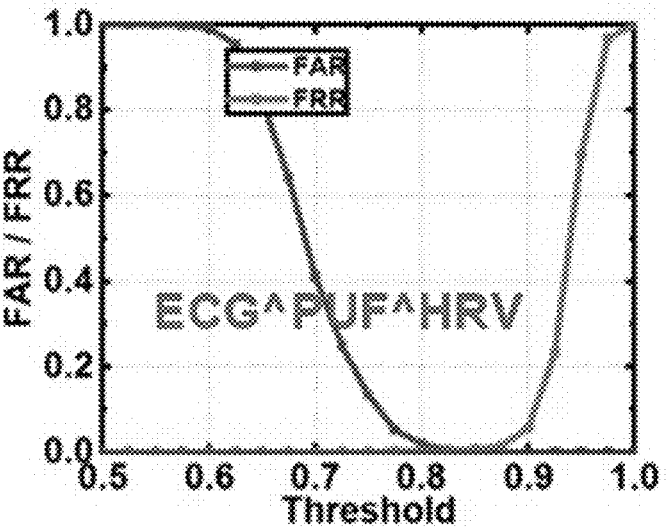
FIG. 11C is a graphical representation of a FAR-FRR plot corresponding to the Hamming distance distribution of FIG. 10C.

FIG. 11A is a graphical representation of a false acceptance rate (FAR)-false rejection rate (FRR) plot corresponding to the Hamming distance distribution of FIG. 10A. FIG. 11B is a graphical representation of a FAR-FRR plot corresponding to the Hamming distance distribution of FIG. 10B. FIG. 11C is a graphical representation of a FAR-FRR plot corresponding to the Hamming distance distribution of FIG. 10C.

Figure 12:
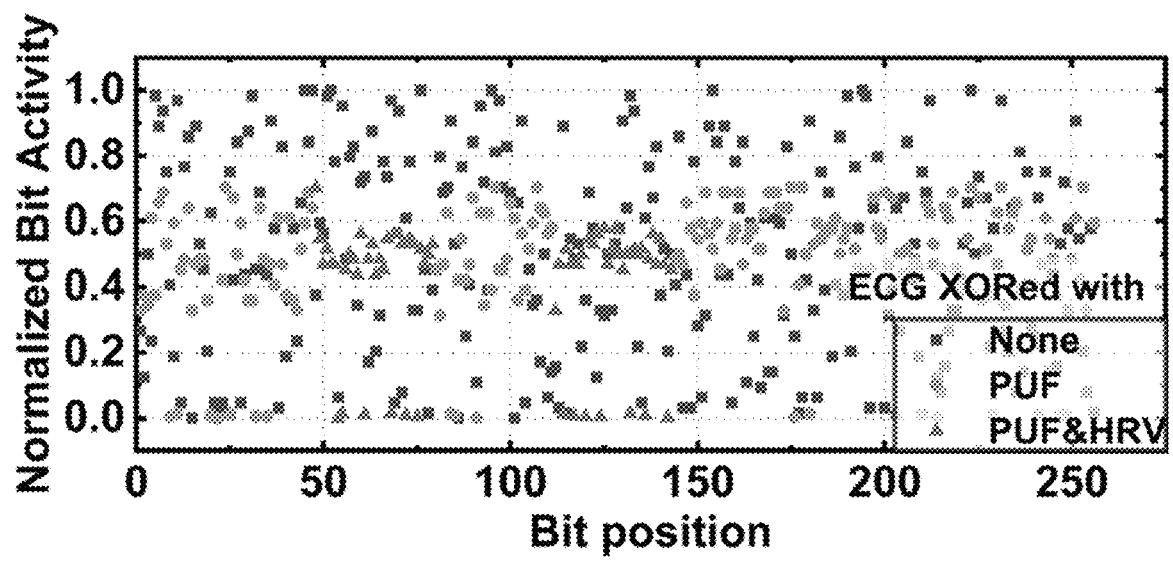
FIG. 12 is a plot showing normalized bit activity for ECG feature vector extraction alone, for ECG feature vector extraction combined with the PUF vector, and for ECG feature vector extraction combined with the PUF vector and HRV.

FIG. 12 is a plot showing normalized bit activity for ECG feature vector extraction alone, for ECG feature vector extraction combined with the PUF vector, and for ECG feature vector extraction combined with the PUF vector and HRV. A bit-position having a normalized activity of 0.5 means that there were approximately equal number of 0s and 1s in that bit-position when taking into account all the feature vectors obtained from the 4 sets of 15 vectors. It is evident that the bit activity factor is improved to close to 0.5 by introducing additional entropy sources such as SRAM PUF and HRV.

Figure 13:
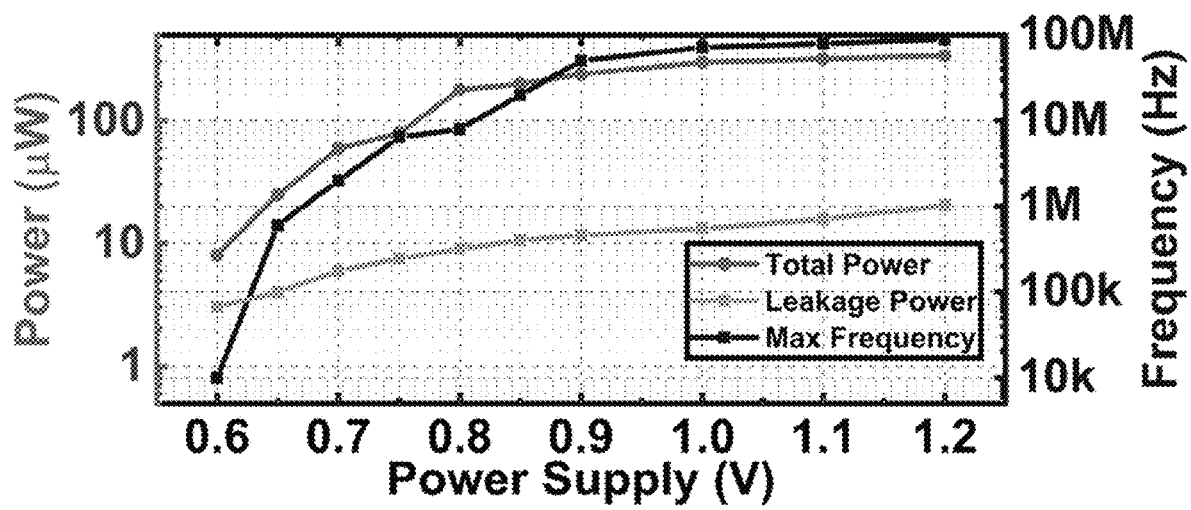
FIG. 13 is a graph showing chip power consumption with voltage and frequency scaling.
Figure 14A:
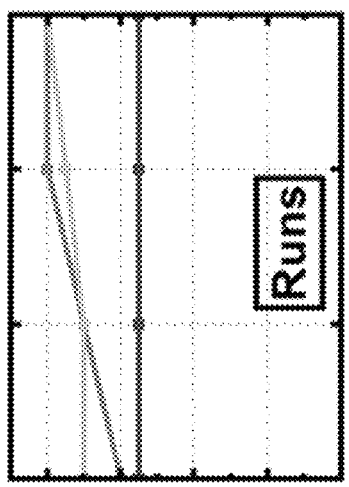
FIGS. 14A-14F are graphical representations illustrating that the number of subjects passing the National Institute of Standards and Technology (NIST) tests out of 16 randomly selected subjects is improved by using multiple entropy sources.
Figure 14B:
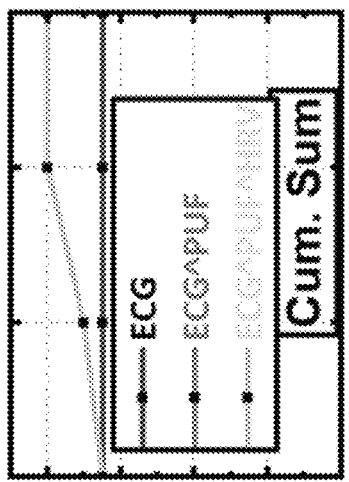
Figure 14C:
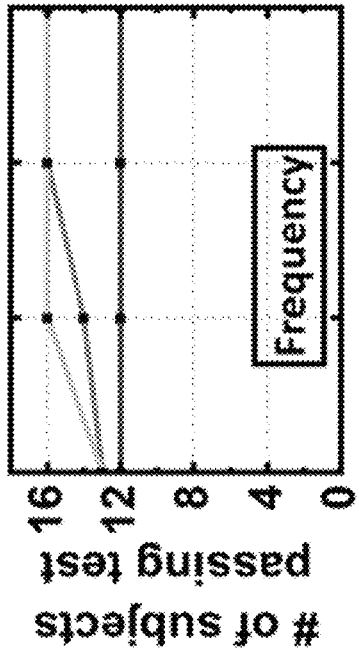
Figure 14D:
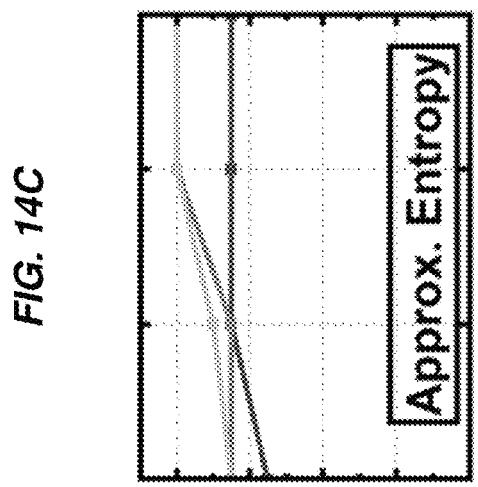
Figure 14E:
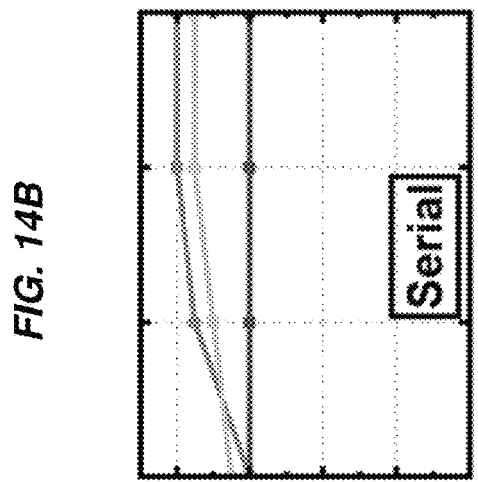
Figure 14F:
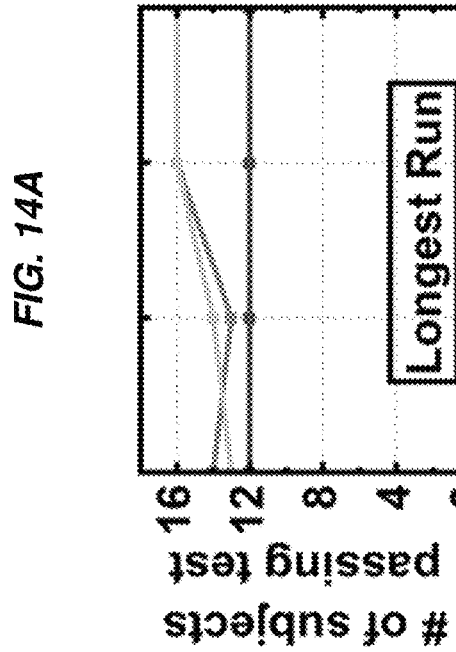

FIG. 13 is a graph showing chip power consumption with voltage and frequency scaling. The total processor power is 8.013 µW at 0.6 V supply and 10 kHz clock frequency. Additionally, the processor can also run 100 times faster at an operating voltage of 0.65 V, consuming thrice the power compared to an operating voltage of 0.6 V. However, such a mode would not be suitable for real-time ECG processing due to the much slower rate of ECG acquisition.

FIGS. 14A-14F are graphical representations illustrating that the number of subjects passing the National Institute of Standards and Technology (NIST) tests out of 16 randomly selected subjects is improved by using multiple entropy sources. Using the obtained sets of random numbers with the three schemes (ECG-only, ECG⊕PUF, and ECG⊕PUF⊕HRV), six NIST randomness tests were performed. A sufficient amount of PUF vectors for 741 subjects were not acquired, therefore 16 subjects were randomly selected from an in-house database. FIGS. 14A-14F show the NIST test results where the randomness is improved after combining the ECG feature vector with PUF and HRV, and shows how different numbers of SRAM PUF bits from 64 and 256 affect the NIST test results.

A comparison with prior hardware security works is shown in Table I. Due to the slow rate of ECG acquisition, latency is larger in ECG schemes compared to conventional security engines in Yang (described in K. Yang et al., "A 23 Mb/s 23 pJ/b fully synthesized true-random-number generator in 28 nm and 65 nm CMOS," in *IEEE Int. Solid-State Circuits Conf. (ISSCC)*, 2014) and Mathew (described in S. K. Mathew et al., "A 0.19 pJ/b PVT-variation-tolerant hybrid physically unclonable function circuit for 100% stable secure key generation in 22 nm CMOS," in *IEEE Int. Solid-State Circuits Conf. (ISSCC)*, 2014). Compared to a previous ECG authentication work Yin (described in S. Yin et al., "A 1.06 µW smart ECG processor in 65 nm CMOS for real-time biometric authentication and personal cardiac monitoring," in *IEEE Symp. on VLSI Circuits*, 2017), EER is reduced by 18.89× (down to 0.09%) by trading off higher power consumption, but the power is still sufficiently low for wearable devices. By optimally integrating three entropy sources of ECG, HRV, and SRAM PUF, the authentication performance and randomness results are substantially improved.

TABLE I

Comparison with Prior Works

|  | Yang | Mathew | Yin | Smart Hardware Security Engine |
|---|---|---|---|---|
| Technology | 65 nm | 22 nm | 65 nm | 65 nm |
| Supply Voltage | N/A | 0.9 V | 0.55 V | 0.6 V |
| Area (mm$^2$) | 0.96 | 24 | 5.94 | 7.54 |
| Power (Digital) | 0.16 mW | 25 µW | 1.06 µW | 8.013 µW |
| Clock Freq. | N/A | 2 GHz | 20 KHz | 10 KHz |
| Memory Size | N/A | N/A | 19.5 kB | 64 kB |
| Entropy Source | TRNG | SRAM | ECG | ECG, SRAM |
| Authentication | No | No | Yes | Yes |
| EER | N/A | 0% | 1.7% | 0.09% |
| Latency (256-bits) | 0.011 ms | N/A | 130 ms | 300 ms |

III. Conclusion

Embodiments of the smart hardware security engine 10 described herein provide a multi-entropy-source authentication and random number generation scheme based on three entropy sources of ECG features, HRV, and SRAM PUF values. The prototype chip (illustrated in FIG. 11) fabricated in 65 nm LP CMOS consumes 8.013 µW at 0.6 V for real-time authentication. Combining three independent entropy sources, the EER of multi-source authentication is reduced down to 0.09% for a large 741-subject in-house database. For 16 randomly selected subjects, PUF values, ECG, and HRV features were optimally combined to generate 256-bit random number per subject, which fully passed the NIST randomness tests.

Those skilled in the art will recognize improvements and modifications to the preferred embodiments of the present disclosure. All such improvements and modifications are considered within the scope of the concepts disclosed herein and the claims that follow.

What is claimed is:

1. A method for biometric authentication, the method comprising:
generating a first biometric feature vector from biometric data, the first biometric feature vector identifying a user;
generating biometric variability data based on the biometric data;
generating a hardware-specific feature vector;
concatenating the first biometric feature vector with the biometric variability data to generate a second biometric feature vector; and
generating a secret key based on the second biometric feature vector and the hardware-specific feature vector.

2. The method of claim 1, wherein generating the first biometric feature vector comprises producing a multi-bit randomized number from the biometric data which differentiates between different users.

3. The method of claim 2, wherein generating the first biometric feature vector further comprises applying a learning algorithm trained to generate the multi-bit randomized number unique to each of the different users.

4. The method of claim 1, further comprising receiving the biometric data through a biometric sensor.

5. The method of claim 4, wherein:
the biometric data comprises cardiac data;
the biometric variability data is an averaged heart rate variability value; and
the biometric sensor comprises at least one of an electrocardiography (ECG) sensor or a photoplethysmography (PPG) sensor.

6. The method of claim 1, wherein the hardware-specific feature vector comprises a physical unclonable function (PUF) vector.

7. The method of claim 1, wherein the secret key is generated to register the user as a registered user.

8. The method of claim 1, wherein the secret key is generated to authenticate a registered user.

9. The method of claim 8, wherein when authenticating the registered user, the first biometric feature vector is extracted over fewer samples of the biometric data than during registration.

10. A circuit, comprising:
hardware-specific feature circuitry capable of producing a hardware-specific feature vector; and
a processor configured to:
receive a biometric signal;
generate biometric variability data based on the biometric signal;
extract a first biometric feature vector from the biometric signal, the first biometric feature vector identifying a user;
concatenating the first biometric feature vector with the biometric variability data to generate a second biometric feature vector; and
generate a secret key based on the second biometric feature vector and the hardware-specific feature vector from the hardware-specific feature circuitry.

11. The circuit of claim 10, wherein the processor comprises a learning algorithm implemented on a neural network to extract the first biometric feature vector.

12. The circuit of claim 11, wherein the neural network is capable of differentiating between biometric signals of different users.

13. The circuit of claim 12, wherein the neural network comprises at least one hidden layer for extracting the first biometric feature vector.

14. The circuit of claim 13, wherein the at least one hidden layer is a fully connected layer.

15. The circuit of claim 13, wherein the at least one hidden layer is a sparsely connected layer.

16. The circuit of claim 13, wherein:

the neural network does not have an output layer; and the first biometric feature vector is based on values of a last layer of the at least one hidden layer.

17. The circuit of claim 16, wherein the neural network is trained by minimizing an application-specific cost function formulated as:

$$\text{cost} = -\frac{\mu_{intra} - \mu_{inter}}{\sigma_{intra} + \sigma_{inter}}$$

wherein $\mu_{intra}$ is a mean of an intra-subject cosine similarity distribution, $\mu_{inter}$ is a mean of an inter-subject cosine similarity distribution, $\sigma_{intra}$ is a standard deviation of the intra-subject cosine similarity distribution, and $\sigma_{inter}$ is a standard deviation of the inter-subject cosine similarity distribution.

18. The circuit of claim 10, wherein the hardware-specific feature circuitry comprises static random-access memory (SRAM) configured to generate a physical unclonable function (PUF) vector.

19. A device, comprising:

a memory; and a processor coupled to the memory and configured to:
  receive biometric data;
  generate biometric variability data;
  extract a first biometric feature vector unique to a user from the biometric data;
  generate a hardware-specific feature vector;
  concatenate the first biometric feature vector with the biometric variability data to generate a second biometric feature vector; and
  authenticate the user based on the second biometric feature vector and the hardware-specific feature vector.

20. The device of claim 19, wherein the device is a wearable device.

21. The device of claim 20, wherein:

the wearable device comprises a cardiac sensor configured to provide the biometric data of the user; and the biometric variability data represents heart rate variability.

22. The device of claim 19, wherein the hardware-specific feature vector comprises a physical unclonable function (PUF) vector.

* * * * *